(12) United States Patent
Feinstein

(10) Patent No.: US 10,485,977 B1
(45) Date of Patent: Nov. 26, 2019

(54) SYSTEM AND METHOD EMPLOYING INTERFERENTIAL ELECTRICAL STIMULATION TO TREAT CARDIAC ISSUES

(71) Applicant: Feinstein Patents, LLC, Wilkes-Barre, PA (US)

(72) Inventor: Peter A. Feinstein, Palm Beach Gardens, FL (US)

(73) Assignee: Feinstein Patents, LLC, Wilkes-Barre, PA (US)

( * ) Notice: Subject to any disclaimer, the term of this patent is extended or adjusted under 35 U.S.C. 154(b) by 0 days.

(21) Appl. No.: 16/022,028

(22) Filed: Jun. 28, 2018

(51) Int. Cl.
*A61N 1/36* (2006.01)
*A61N 1/32* (2006.01)
*A61N 1/04* (2006.01)
*A61B 5/0408* (2006.01)
*A61B 5/00* (2006.01)
*A61N 1/378* (2006.01)

(52) U.S. Cl.
CPC ........ *A61N 1/36114* (2013.01); *A61B 5/0033* (2013.01); *A61B 5/0408* (2013.01); *A61N 1/0452* (2013.01); *A61N 1/0456* (2013.01); *A61N 1/323* (2013.01); *A61N 1/36053* (2013.01); *A61N 1/378* (2013.01)

(58) Field of Classification Search
CPC .............. A61N 1/36114; A61N 1/0452; A61N 1/36053; A61N 1/378; A61N 1/0456; A61N 1/323; A61B 5/0408; A61B 5/0033
See application file for complete search history.

(56) References Cited

U.S. PATENT DOCUMENTS

| 5,324,317 | A | | 6/1994 | Reiss |
| 5,512,057 | A | | 4/1996 | Reiss et al. |
| 5,776,173 | A | * | 7/1998 | Madsen, Jr. ....... A61N 1/36021 607/67 |
| 6,564,103 | B2 | | 5/2003 | Fischer et al. |
| 8,401,637 | B2 | | 3/2013 | Kroll et al. |
| 8,467,880 | B2 | | 6/2013 | Glukhovsky et al. |

(Continued)

FOREIGN PATENT DOCUMENTS

| CN | 102614579 | 8/2012 |
| DE | 3546381 | 7/1987 |

*Primary Examiner* — Rex R Holmes
(74) *Attorney, Agent, or Firm* — Forge IP, PLLC

(57) ABSTRACT

An interferential current system for cardiac treatment of a patient, includes a controller, a stimulation power supply and a plurality of electrodes. The electrodes supply transcutaneous electrical impulses when supplied power by the stimulation power supply, the plurality of electrodes including at least two electrodes supplying transcutaneous electrical impulses at two different frequencies, the transcutaneous electrical impulses provided at two different frequencies giving rise to at least one beat impulse having an interference frequency. At least one sensor in communication with the controller provides data to the controller indicative of various cardiac pathologic conditions, including but not limited to, rhythm abnormalities, muscle wall contraction abnormalities, and ischemic heart disease abnormalities of the patient. At least one of a timing and an intensity of the transcutaneous electrical impulses is varied by the controller based at least in part upon the data indicative of the aforementioned cardiac pathologies of the patient.

14 Claims, 5 Drawing Sheets

(56) References Cited

U.S. PATENT DOCUMENTS

| | | |
|---|---|---|
| 8,718,759 B2 | 5/2014 | Kroll |
| 8,750,990 B1 | 6/2014 | Gilman et al. |
| 8,805,495 B2 | 8/2014 | Gilman et al. |
| 9,713,727 B2 | 7/2017 | Kroll |
| 2007/0299895 A1 | 12/2007 | Johnson et al. |
| 2011/0125225 A1* | 5/2011 | Lakshimanan ...... A61N 1/3625 607/67 |
| 2014/0194949 A1 | 7/2014 | Wichner |
| 2017/0028189 A1 | 2/2017 | Stanley |

* cited by examiner

SYSTEM AND METHOD EMPLOYING INTERFERENTIAL ELECTRICAL STIMULATION TO TREAT CARDIAC ISSUES

FIELD OF THE INVENTION

The invention relates to system employing the use of an electrical stimulator, such as an Interferential Current (IFC) device, or other type of deep penetration electrical stimulation that is non-invasive and external (i.e., transcutaneous), for treating a variety of cardiac issues. For example, the system may be used for pacing a patient's heart to treat cardiac rhythm abnormalities instead of employing an implantable pacemaker (or until an implantable pacemaker can be surgically inserted), may be used as a percutaneous heart failure treatment as part of a cardiac contractility modulation treatment regime and may be used to treat pathology related to or causing ischemic heart disease, myocardial infarction, and other cardiac vascular issues.

BACKGROUND OF THE INVENTION

Various types of electrical stimulation have been known to be used for various therapeutic purposes for millennia, tracing all the way back to Roman times when physicians treated patients suffering from pain and acute gout with electric rays and other electrically-charged sea creatures. Since that time, many medical uses for electrical stimulation have been developed, with one of the most important and prevalent uses in modern times being embodied in cardiac pacemakers.

Cardiac pacemakers stimulate cardiac activity in a patient by delivering periodic electrical pulses through electrodes to the patient's heart. The electrical pulses cause electrical depolarization and subsequent cardiac contraction to assist the heart in beating at a desired rhythm. There are many different varieties of cardiac pacemaker systems. In general, cardiac pacemaker systems are categorized according to the location of the electrodes and the pathway that the electrical stimulus travels to the heart.

The earliest wearable pacemakers were "epicardial" pacing systems, wherein electrodes are placed on the surface of the heart. While these types of pacemakers are still in widespread use in certain circumstances, other types of pacemakers have also been developed and widely used. For example, "transvenous" pacemaker systems use electrodes mounted on catheters that are maneuvered through large central veins to the right ventricle or right atrium of the heart, while "transesophageal" pacing systems employ electrodes located in the esophagus. Another type of pacemaker is the "transcutaneous" cardiac pacemaker system, which delivers pacing impulses to the heart through the patient's skin using cutaneous electrodes (i.e., electrodes externally attached to the skin of the patient).

The present invention invention concerns the transcutaneous type of cardiac pacing systems, as well as other types of transcutaneous cardiac treatment systems not related to pacing.

Transcutaneous pacing is commonly used in emergency medicine for immediate treatment of unstable bradycardia, a condition in which the heart is beating too slowly and/or irregularly. Since the electrodes are attached externally to the skin, the transcutaneous pacing can be applied immediately to a heart troubled patient without intervention, and thereby have traditionally served as a therapeutic bridge until a transvenous or other type of implantable pacemaker could be established under more controlled circumstances.

One of the drawbacks with traditional transcutaneous pacing, however, is that patients may experience discomfort. More specifically, the discomfort may be in the form of a muscular skeletal pain induced from electrical skin and muscle stimulation. Depending upon the patient's own tolerance level and the current required for rhythm capture in the specific situation, this discomfort might range from moderate and tolerable to severe and intolerable. Typically, the applied current will be set at 10 milliamps to start and then be increased by increments of 10 until rhythm capture is noted. At that point, the pacing system current will then typically be set at a current of about 1.25 times what was required for capture. It has been found that most patients cannot tolerate currents of 50 milliamps and higher without sedation, while often 50-100 milliamps are required. Thus, practitioners are encouraged to strongly consider sedation in connection with traditional transcutaneous pacing systems, and even then, with long term use, burns are not uncommon.

While the relatively high direct currents necessary for pacing using traditional transcutaneous pacemakers may be unavoidable in some situations (e.g., where there is serious damage to the electrical systems of the heart), there are other situations where such high currents may not be required. For example, in cases of ventricular tachycardia, the heart may beat very rapidly and inefficiently (for example at a rate of 150 beats per minute or more). Moreover, it is known that arrhythmic ventricular fibrillation often occurs in a fatal heart attacks, and it may be desirable to specifically treat this condition instead of or in addition to the application of a direct current shock from a defibrillator.

In such situations involving arrhythmias, it has been found that stimulation of the cardiac branches of the vagus nerve may allow for the desired results to be achieved. The vagus nerve, which is the main parasympathetic nerve of the body and is outside of the spinal cord, regulates heart rate. Increased vagal activity slows the heart down. Thus, through secondary effect on the cardiac branches of the vagus nerve as opposed to direct effect on the SA and AV nodes, cardiac rhythm may be slowed, for example, in ventricular tachycardia, from an inefficient 150 beats per minute down to 60 beats per minute as part of initial treatment by the cardiologist.

A similar approach can be used to slow down the arrhythmic ventricular fibrillation that often occurs in a fatal heart attack to perhaps augment a direct current shock from a defibrillator by keeping the heart rate slow and controlled so as not to have to re-shock the patient, thereby employing not only direct electrical stimulation of the heart muscle itself, but also employing vagus nerve control of the heart.

Another similar approach is to affect the muscular contracture to the atrium in order to treat atrial fibrillation on a short term basis acting as a temporary substitute or bridge until a regular pacemaker can be inserted.

What is desired, therefore, is an external cardiac pacing system that may be used in certain appropriate situations instead of or in addition to traditional transcutaneous pacemaker systems, that can be applied immediately to a heart troubled patient, but that does not suffer from the disadvantages of such traditional systems (i.e., causing discomfort, thereby often necessitating sedation, and possibly causing skin damage).

Also desired is a replacement for other cardiac treatment systems that require surgical implantation of leads, with consequently similar disadvantages, as compared to implantable cardiac pacemaker systems.

For example, research and development is currently underway to alleviate problems associated with heart failure using electrical stimulation by way of a technique known as cardiac contractility modulation (CCM). The short- and long-term use of this therapy has been found to enhance the strength of ventricular contraction and therefore the heart's pumping capacity by modulating (adjusting) the myocardial contractility.

More specifically, in CCM therapy, electrical stimulation is applied to the cardiac muscle during the absolute refractory period. In this phase of the cardiac cycle, electrical signals cannot trigger new cardiac muscle contractions, hence this type of stimulation is known as a non-excitatory stimulation. However, the electrical signals increase the influx of calcium ions into the cardiac muscle cells (cardiomyocytes). In contrast to other electrical stimulation treatments for heart failure, such as pacemaker therapy or implantable cardioverter defibrillators, CCM does not affect the cardiac rhythm directly. Rather, the aim is to enhance the heart's natural contraction (the native cardiac contractility) sustainably over long periods of time. Furthermore, unlike most interventions that increase cardiac contractility, CCM is not associated with an unfavorable increase in oxygen demand by the heart. This may be explained by the beneficial effect the therapy has in improving cardiac efficiency.

A meta-analysis in 2014 and an overview of device-based treatment options in heart failure in 2013 concluded that CCM treatment is safe, that it is generally beneficial to patients and that the treatment increases the exercise tolerance and quality of life of patients. Furthermore, preliminary long-term survival data shows that CCM treatment is associated with lower long-term mortality in heart failure patients when compared with expected rates among similar patients not treated with CCM.

However, traditional CCM treatment options do suffer from disadvantages, which disadvantages are similar to those associated with traditional pacemakers. Specifically, traditional CCM treatment options involve either the surgical placement of leads on or in the heart, or involve the application of relatively high current transcutaneously, which can cause patient discomfort, thereby possibly necessitating sedation, and which can cause skin damage.

Thus, what is also desired, is an external CCM treatment system that maintains the benefits of traditional CCM treatment systems, but that does not suffer from the disadvantages of such traditional systems (i.e., either requiring surgical intervention in the case of implantable systems or causing discomfort, thereby often necessitating sedation, and possibly causing skin damage in the case of transcutaneous systems).

Similarly, cardiac ultrasounds are often used to noninvasively identify ventricular wall inappropriate contraction or lack of contraction, signifying a prior myocardial infarction where the muscle is now no longer working correctly. An external treatment system is desired that can be used to stimulate blood flow to scarred or devitalized cardiac tissue to help the muscle that is still alive to contract in a more normal fashion with the rest of the ventricle. Similarly, such stimulation of blood flow to an area of marginally compromised but not yet devitalized cardiac muscle would help muscle in that situation to heal more effectively and with less malfunctioning scar tissue. The increased circulation provided by the invention can also be utilized to help stimulate and promote an environment conducive to stem cell survival or to successful implementation of other alternative treatments currently being investigated to grow new cardiac tissue in damaged areas of the heart.

Further desired is an external cardiac treatment system that may be used to assist in the treatment of ischemic heart disease, angina, and consequences from acute myocardial infarction. Such a system is also desired to be used in connection with assisting with cardiac stenting and promoting better outcomes for treatment of stenosed coronary arteries.

Millions of EKGs are done in doctor's offices on a daily basis as a screening test for coronary artery disease and ischemic heart disease to pre-emptively identify these situations and treat them before there is a myocardial infarction and actual cardiac muscle death, dysfunction, and congestive heart failure, or death from a myocardial infarction.

One of the ways that angina and ischemic heart disease is treated, when present on a chronic or crescendo basis over time, is with sublingual nitroglycerin, which is a coronary artery vasodilator, and also decreases "afterload" on the heart in terms of left ventricular pumping. This makes it easier for the heart to pump at a lower blood pressure because of vasodilatation from the aorta distally in terms of pushback or resistance from vascular abnormal afterload. Afterload is a term commonly used to describe arteriosclerotic vascular disease and hypertension as conditions either independent of each other or found in combination with each other, that force the heart to pump more aggressively at a higher blood pressure in order to deliver blood to the rest of the body. By decreasing the afterload with nitroglycerine, or any type of antihypertensive pharmacologic agent, this increased workload for the heart is diminished on a temporary basis, allowing the heart to get more oxygen, work less hard, and hopefully diminish the pain and symptoms associated with angina while protecting the heart from a myocardial infarction and cell death.

However, it should be noted that all of the medications used to treat acute myocardial infarctions and ischemic heart disease in acute and chronic stages, such as antihypertensive medications and medications that decrease afterload, have associated pharmacological side effects that can potentially be life threatening in their own right.

Screening EKGs in doctor's offices are used to see if there is an area of the heart that is ischemic, even though there may not be symptomatology from it. This is reflected in an inverted T-wave in any one of the EKG leads. When a cardiologist notes a new inverted T-wave or change in a patient's EKG taken as a diagnostic screening measure, he/she needs to assess the status of the coronary artery that goes to the area of the heart that correlates anatomically with the abnormal EKG, and to consider performing a cardiac catheterization to determine if there is a stenosis serious enough to result in, or evolve into, a life threatening situation. Depending on the data from the EKG and the more advanced and invasive medical work up of the situation, the cardiologist must consequently determine whether a stent or pharmacologic treatments or a combination of both, as described above, will help.

It would be desirable to be able target the ischemic area of the heart identified by the inverted T-wave on EKG and other diagnostic studies, for vasodilatation treatment in order to increase blood flow to that particular ischemic area on a small vessel basis, and even target whichever major coronary artery that supplies the identified area, treating it with transcutaneous electrical stimulation while waiting for a stent to be placed. Targeting the stenotic area of a main coronary artery with transcutaneous electrical stimulation to cause it to vasodilate would allow for protection of the heart while treatment is undertaken. Such a system may be used in conjunction with various pharmacologic agents so as to work synergistically with those agents to decrease cardiac afterload, or it would provide treatment during the time frame waiting for such medications to take effect, or in some cases, such a system may be used instead of pharmacologic agents to avoid deleterious side effects.

SUMMARY OF THE INVENTION

It has been found that the lower the stimulation frequency of an electrical current, the greater the resistance to the passage of the current through the skin and other body tissues, leading to potentially significant discomfort being experienced by the patient. The skin's impedance at 50 Hz is approximately 3200 ohms, while at 4000 Hz it is reduced to approximately 40 ohms. The result of applying this latter frequency is that it will pass more easily through the skin and any other tissues before hitting the target tissue or organ. However, it has also been found that medium frequency current (e.g., 4000 Hz) generally does not have the beneficial therapeutic effects as does the much lower frequency currents typically employed by traditional electrical stimulation modalities (e.g., 125 Hz).

Interferential current (IFC therapy) is a unique and separate form of electrical therapeutic stimulation that expands the scope and capabilities for medical intervention in situations not amenable other forms of electrical therapy. In general, IFC therapy utilizes two or more medium frequency currents which pass through body tissues simultaneously. They are set up so that their paths cross; and in simple terms they interfere with each other (hence the name "interferential" current therapy). This interference gives rise to an interference or beat frequency, which has the characteristics of low-frequency stimulation. The exact frequency of the resultant beat frequency can be controlled by the input frequencies. For example, if one current is at about 4000 Hz and the other current is at about 3900 Hz, the resultant beat frequency would be at about 100 Hz.

Thus, the basic principle of IFC therapy is to utilize the strong physiological effects of the low frequency electrical stimulation of muscle and nerve tissues at sufficient depth, without the associated painful and unpleasant side effects of such low frequency stimulation. The medium frequency currents penetrate the tissues with very little resistance, whereas the resulting interference current (low frequency) is in the range that allows effective stimulation of the biological tissues. The resistance (impedance) of the skin is inversely proportional to the frequency of the stimulating current. Thus, the therapeutic beat frequency of IFC results in the desired physiologic response from the target organ or tissue, while requiring less electrical energy input to the deeper tissues than would be required if a single low frequency current was employed, giving rise to less discomfort.

In a broad sense, the present invention employs this IFC technology in the context of various cardiac therapies in order to achieve beneficial results of known techniques, while avoiding many of the disadvantages thereof.

In one respect, the present invention is directed to an interferential current system for cardiac treatment of a patient, including a controller, a stimulation power supply in communication with the controller and a plurality of electrodes in electrical communication with the stimulation power supply, the plurality of electrodes supplying transcutaneous electrical impulses when supplied power by the stimulation power supply. The plurality of electrodes comprises at least two electrodes supplying transcutaneous electrical impulses at two different frequencies, the transcutaneous electrical impulses provided at two different frequencies giving rise to at least one beat impulse having an interference frequency. A sensor in communication with the controller provides data to the controller indicative of cardiac contractions of the patient, and at least one of a timing and an intensity of the transcutaneous electrical impulses is varied by the controller based at least in part upon the data indicative of cardiac contractions of the patient.

In some embodiments, the cardiac treatment comprises cardiac pacing, and the plurality of electrodes are disposed so as to stimulate a vagus nerve of the patient. In some embodiments, the cardiac treatment comprises vasodilation, and the sensor comprises an electrocardiography sensor, whereby an ischemic area of the heart is identified. In some embodiments, the interference frequency is within a range from 10-150 Hz and is disposed so as to stimulate a parasympathetic nerve.

In some embodiments, the cardiac treatment comprises cardiac contractility modulation (CCM), and the plurality of electrodes are disposed so as to stimulate heart contractions at predetermined times during a heartbeat cycle. In certain of these embodiments, the timing of the transcutaneous electrical impulses is varied based at least in part upon the data indicative of cardiac contractions of the patient such that electrical stimulation is applied to the cardiac muscle during an absolute refractory period of the heartbeat cycle.

In some embodiments, the sensor comprises an electrocardiogram (EKG) sensor.

In some embodiments, the controller generates a patient specific model based at least in part on the data indicative of cardiac contractions of the patient. In certain of these embodiments, the system further comprises an imaging sensor, and the patient specific model is further based at least in part on imaging data received from the imaging sensor. In certain embodiments, the patient specific model is indicative of electrode placement appropriate for the transcutaneous electrical impulses to reach a desired therepautic target area. In certain embodiments, the imaging sensor comprises an imaging sensor employing at least one of the following modalities: ultrasound, Level II ultrasound, 3D ultrasound, 4D ultrasound, trans esophageal echogram (TEE), x-rays, computed tomography (CT) scanning, magnetic resonance imaging (MRI) scanning, 3D magnetic resonance imaging (MRI) scanning, positron emission tomography (PET), radiography, elastography, plethsmethography, thermography, bone scanning and image intensification In some embodiments, the patient specific model is indicative of appropriate magnitudes of the at least two different frequencies. In certain embodiments, the patient specific model is indicative of the appropriate interference frequency.

In some embodiments, the plurality of electrodes comprises: a first electrode supplying transcutaneous electrical impulses at a first frequency and a second electrode supplying transcutaneous electrical impulses at a second frequency different than the first frequency, the transcutaneous electrical impulses provided at the first and second frequencies giving rise to a first beat impulse having a first interference frequency stimulating a first area of a heart of the patient; and a third electrode supplying transcutaneous electrical impulses at a third frequency and a fourth electrode supplying transcutaneous electrical impulses at a fourth frequency different than the third frequency, the transcutaneous electrical impulses provided at the third and fourth frequencies giving rise to a second beat impulse having a second interference frequency stimulating a second area of the heart of the patient.

In accordance with another aspect of the present invention, a method for cardiac treatment of a patient employing interferential current therapy comprises the steps of: (i) disposing a plurality of electrodes on an epidermis of a patient; (ii) supplying to a heart of the patient, with the plurality of electrodes, transcutaneous electrical impulses at two different frequencies, the transcutaneous electrical impulses provided at two different frequencies giving rise to at least one beat impulse having an interference frequency; (iii) collecting sensor data indicative of cardiac contractions of the patient; and (iv) varying at least one of a timing and an intensity of the transcutaneous electrical impulses based at least in part upon the data indicative of cardiac contractions of the patient.

The embodiments as discussed above are illustrative and are not intended to exhaust all possible arrangements, modifications, and variations of features of the invention.

DETAILED DESCRIPTION OF THE INVENTION

Figure 1:
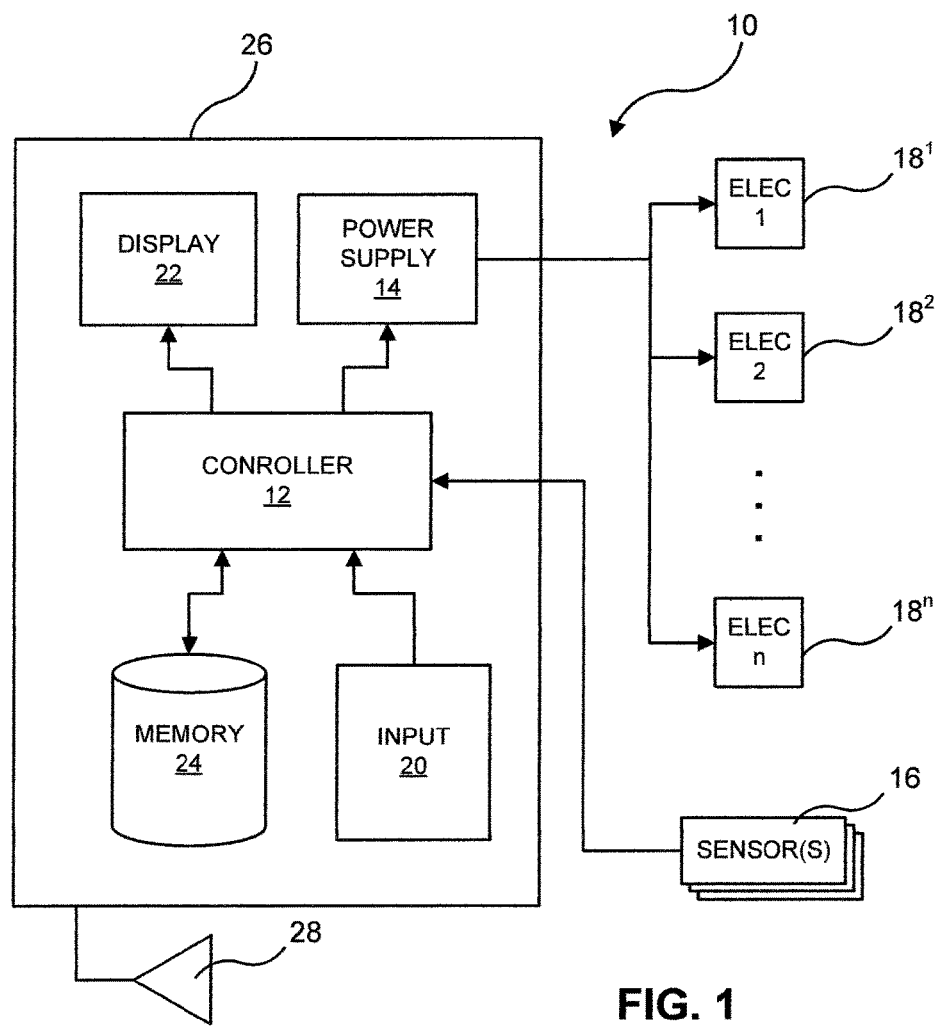
FIG. 1 is a block diagram schematically illustrating a transcutaneous cardiac treatment device employing interferential current (IFC) therapy, according to an exemplary embodiment of the present invention.

Referring now to the Figures and first to FIG. 1, there is shown an exemplary embodiment of a device (10) for performing various therapeutic treatments on a patient (50). The device (10) includes a controller (12), a stimulation power supply (14) in communication with the controller (12) and one or more sensors (16) providing sensor feedback to the controller (12). The device (10) also includes a plurality of electrodes ($18^1, 18^2 \ldots 18n$) in electrical communication with the stimulation power supply (14). As will be explained in more detail below, the controller (12), the stimulation power supply (14) and the electrodes ($18^1, 18^2 \ldots 18n$) are particularly configured to employ interferential current (IFC) therapy, while the controller (12) and the one or more sensors (16) are configured to provide feedback and/or targeting capabilities to monitor the heartbeat of the patient and/or ensure that the stimulating currents are directed to the appropriate areas of the patient's body to achieve the desired results.

The plurality of electrodes ($18^1, 18^2 \ldots 18n$) are disposed on an epidermis (52) of the patient (50) and are arranged to supply transcutaneous electrical impulses that cause the desired cardiac reactions depending on the specific type of cardiac therapy being employed, as explained in more detail below. Various options are possible for electrode ($18^1, 18^2 \ldots 18n$) placement, as well as types of electrodes used, also as is explained in more detail below.

The controller (12) causes the stimulation power supply (14) to supply power to the plurality of electrodes ($18^1, 18^2 \ldots 18n$) according to a programmed set of parameters, again depending on the targeted area and the desired response to be elicited.

The device (10) also includes an input mechanism (20) (such as a keyboard, touchscreen, joystick or the like) as is known in the art, which allows the user to enter control parameters and the like. As but one example, input mechanism (20) may include a button or other type of controller to turn the device on or off manually, to trigger the stimulation power supply (14), to set a target heart rate for the patient, etc. Another example allowing greater flexibility and ease of use is based on a mobile device (such as a cellphone) or mobile device (e.g., cellphone) app. Such an app might also have the ability to notify a patient or a healthcare provider that the sensors are accumulating data indicating that at a specific time the user has to activate the IFC device as in an alarm for manual use by the user. Similarly, such a program could automatically turn on the device at a specific time for a specific reason without any input from the person being treated.

Also as is well known in the art, the device (10) includes a display (22) to provide visual and/or auditory output to the patient and/or another user of the device (10) (e.g., a medical professional). The display (22) may also present the patient/user with other helpful information. For example, the device (10) may be linked to a mapping app on a mobile device (such as Google maps or Waze) in order to display or otherwise provide information concerning appropriate healthcare or other public facilities.

In some embodiments the system further includes the ability to transmit information and data obtained via the Internet or other mechanism to remote or off site locations for consultation or expert input, interpretation, and monitoring of data garnered during or after the procedure, or for incorporation into electronic medical records (EMRs), or for telehealth applications.

The device may further include an antenna (28) or the like (such as Bluetooth functionality) in order to provide connectivity to a mobile network or direct connectivity to a mobile phone, computerized fitness tracker, smart watch, etc. The antenna (28) or the like may also be used to provide wireless connectivity for the sensor(s) (16) rather than employing a wired connection.

The device (10) further includes a memory (24), which allows the device to store various parameters that may be employed by the controller (12).

The controller (12), stimulation power supply (14), input mechanism (20), display (22), memory (24) and antenna (28) may be contained in a housing (26), as should be apparent to those skilled in the art. Various types of connectors may be provided on the housing to allow for connection of the electrodes ($18^1, 18^2 \ldots 18n$), the sensor (16), or various other devices (e.g., mobile phones, tablets, smart watches, etc.) also as should be apparent to those skilled in the art.

As discussed above, the present invention is particularly adapted to employ interferential current (IFC) technology. Also as discussed above IFC therapy generally utilizes two medium frequency currents which pass through the tissues simultaneously. They are set up so that their paths cross; and in simple terms they interfere with each other. This interference gives rise to an interference or beat frequency, which has the characteristics of low-frequency stimulation. The exact frequency of the resultant beat frequency can be controlled by the input frequencies. For example, if one current is at about 4000 Hz and the other current is at about 3900 Hz, the resultant beat frequency would be at about 100 Hz.

Figure 2:
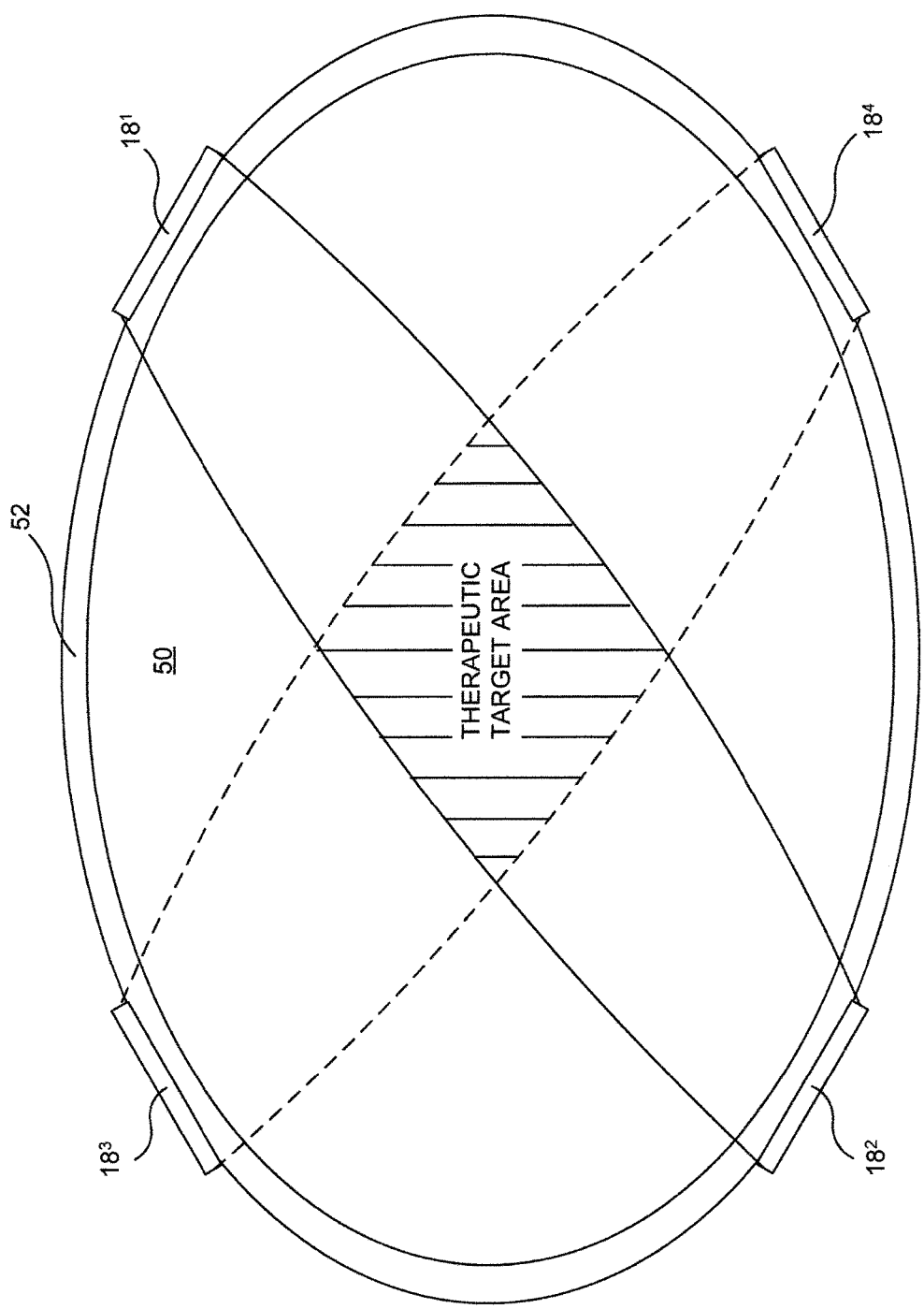
FIG. 2 is schematic view illustrating rudimentary operational characteristics of the device shown in FIG. 1.

Referring now to FIG. 2, an exemplary arrangement of electrodes employing IFC therapy is shown applied to the epidermis (52) of a patient (50). In this example, a first pair of electrodes ($18^1$, $18^2$) supplies transcutaneous electrical impulses at a first frequency (represented by solid lines) and a second pair of electrodes ($18^3$, $18^4$) supplies transcutaneous electrical impulses at a second frequency (represented by dashed lines) different than the first frequency. The transcutaneous electrical impulses provided at the first and second frequencies giving rise to a beat impulse in a therapeutic target area (located at the position shown in FIG. 2 where the area defined by solid lines and the area defined by dashed lines overlap, as highlighted with vertical cross-hatching) having an interference frequency.

The beat impulse is controlled depending on the type of nerve/tissue/organ to be stimulated, as well as on real-time feedback of the elicited response (as explained in more detail below). For example, it has been found that beat impulses having a frequency in the range of from 1-5 Hz may provide desirable stimulation properties for sympathetic nerves, beat impulses having a frequency in the range of from 10-150 Hz may provide desirable stimulation properties for parasympathetic nerves, beat impulses having a frequency in the range of from 10-50 Hz may provide desirable stimulation properties for motor nerves, beat impulses having a frequency in the range of from 90-100 Hz may provide desirable stimulation properties for sensory nerves, beat impulses having a frequency in the range of from 90-150 Hz may provide desirable stimulation properties for nociceptive fibers, and beat impulses having a frequency in the range of from 1-10 Hz may provide desirable stimulation properties for smooth muscle. As will be recognized, other types of nerves/tissues/organs may respond to other beat impulse frequencies.

As has been recognized, some types of nerves, tissues, organs and/or muscles will sometimes acclimate to a constant signal. Accordingly, in some embodiments, the electrodes vary the beat frequency, either automatically or upon user input from a medical practitioner, to produce a frequency "sweep" that avoids this problem.

Figure 3:
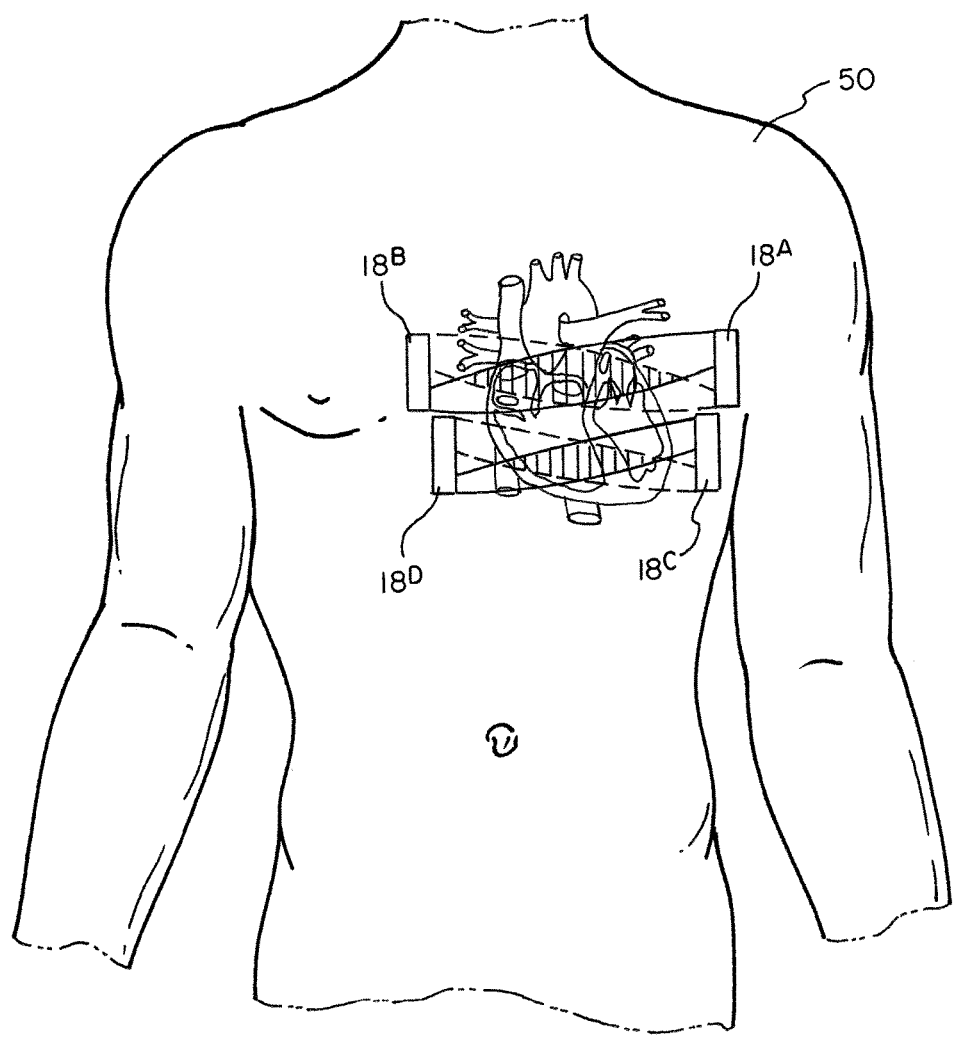
FIG. 3 is schematic view illustrating the device shown in FIG. 1 being used on a patient.

Turning now to FIG. 3, an exemplary positioning of the electrodes ($18^A$-$18^D$) on the patient (50) is shown.

As is known, the heart is basically a pump made up of muscle tissue that is stimulated by electrical currents, which normally follow a specific circuit within the heart. This normal electrical circuit begins in the sinus or sinoatrial (SA) node, which is a small mass of specialized tissue located in the right atrium (upper chamber) of the heart. The SA node generates an electrical stimulus at 60 to 100 times per minute (for adults) under normal conditions; this electrical impulse from the SA node starts the heartbeat.

The electrical impulse travels from the SA node via the atria to the atrioventricular (AV) node in the bottom of the right atrium. From there the impulse continues down an electrical conduction pathway called the Bundle of His and then on through the "His-purkinje" system into the ventricles (lower chambers) of the heart. When the electrical stimulus occurs it causes the muscle to contract and pump blood to the rest of the body. This process of electrical stimulation followed by muscle contraction is what makes the heartbeat.

The electrical circuit of the heart overall is controlled by the vagus nerve, which is the main parasympathetic nerve of the body and is outside of the spinal cord. The vagus nerve regulates heart rate. In general, increased vagal activity slows the heart down. For example, in cases of ventricular tachycardia, the heart may beat very rapidly and inefficiently (for example at a rate of 150 beats per minute or more). Moreover, it is known that arrhythmic ventricular fibrillation often occurs in a fatal heart attacks.

In both of these situations, it has been found that stimulation of the vagus nerve may allow for the desired results to be achieved. Thus, through secondary effect on the vagus nerves employing an IFC scheme using the electrodes ($18^A$-$18^D$), as opposed to direct effect on the SA and AV nodes, cardiac rhythm may be slowed, for example, in ventricular tachycardia, from an inefficient 150 beats per minute down to 60 beats per minute as part of initial treatment by the cardiologist to save the patient's life.

A similar approach of stimulating the vagus nerve employing IFC and electrodes ($18^A$-$18^D$) can be used to be used to slow down the arrhythmic ventricular fibrillation that often occurs in a fatal heart attack to perhaps augment a direct current shock from a defibrillator keeping the heart rate slow without re-shocking the patient, thereby employing not only direct electrical stimulation of the heart muscle itself, but also employing vagus nerve control of the heart.

In each of these cases employing IFC to stimulate the vagus nerve, the interference frequency may desirably be set within a range from 10-150 Hz, which has been found to provide desirable stimulating properties on parasympathetic nerves, such as the vagus nerve.

Similarly, stimulation using an IFC scheme through electrodes) ($18^A$-$18^D$) can be used to affect the muscular contracture to the atrium in order to treat atrial fibrillation on a short term basis, acting as a temporary solution until a regular pacemaker can be inserted.

In the exemplary embodiment of FIG. 3, a first electrode ($18^A$) supplies transcutaneous electrical impulses at a first frequency and a second electrode ($18^B$) supplies transcutaneous electrical impulses at a second frequency different than the first frequency, the transcutaneous electrical impulses provided at the first and second frequencies giving rise to a first beat impulse having a first interference frequency. As but one non-limiting example, when the system (10) is being used for pacing purposes, the first and second electrodes ($18^A$,$18^B$) may be positioned such the Therapeutic Target Area thereof (shown with vertical cross-hatching) is positioned to cause stimulation of the vagus nerve, which will in turn affect the heartbeat of the patient. The electrodes may be automatically activated to generate and vary the stimulus until a desired heart rate is achieved.

In accordance with another aspect of the present invention, the system (10) may be used to assist in the treatment of ischemic heart disease, angina, and consequences from acute myocardial infarction. Such a system may also be used in connection with assisting with cardiac stenting for stenosed coronary arteries.

As discussed above, one of the ways that angina and ischemic heart disease is treated, when present on a chronic or crescendo basis over time, is with sublingual nitroglycerin, which is a coronary artery vasodilator, and also decreases "afterload" on the heart in terms of left ventricular pumping. This makes it easier for the heart to pump at a lower blood pressure because of vasodilatation from the aorta distally in terms of pushback or resistance from vascular abnormal afterload.

The system (10) of the present invention may be used instead of, or in addition to, sublingual nitroglycerin, to act as coronary artery vasodilator (or vasodilator for other relevant blood supplies). Advantageously, the system may employ EKG sensor data to identify one or more areas of the heart that is/are ischemic, and then an appropriate number of electrodes may be employed.

For example, referring specifically to the exemplary embodiment shown in FIG. 3, two sets of electrodes may be employed if two ischemic areas are identified. First and second electrodes ($18^A, 18^B$) may be positioned such that the Therapeutic Target Area thereof (shown with vertical cross-hatching) is positioned to cause stimulation resulting in vasodilation of a blood supply affecting a first ischemic area. A third electrode ($18^C$) may further supply transcutaneous electrical impulses at a third frequency and a fourth electrode ($18^D$) may supply transcutaneous electrical impulses at a fourth frequency different than the third frequency, the transcutaneous electrical impulses provided at the third and fourth frequencies giving rise to a second beat impulse having a second interference frequency. The third and fourth electrodes ($18^C, 18^D$) are positioned such the Therapeutic Target Area thereof (shown with vertical cross-hatching) is positioned to cause stimulation resulting in vasodilation of a blood supply affecting a second ischemic area.

Since it is generally the case that vasodilation of blood supplies can generally be achieved by stimulating parasympathetic nerves, it may be desirable for the first and second interference frequencies to be set within a range from 10-150 Hz. In alternative embodiments, it may be desirable to instead stimulate heart muscle directly, in which case it may be desirable to use different interference frequencies, such as interference frequencies within the range of 1-10 Hz which is known to provide desired stimulation in muscles.

As discussed above, in another example of the present invention, first and second electrodes ($18^A, 18^B$)—and optionally third and fourth electrodes ($18^C, 18^D$)—may be positioned such that the Therapeutic Target Area(s) thereof (shown with vertical cross-hatching) is/are positioned to cause the stimulation necessary for cardiac contractility modulation (CCM) therapeutic treatment.

Figure 4B:
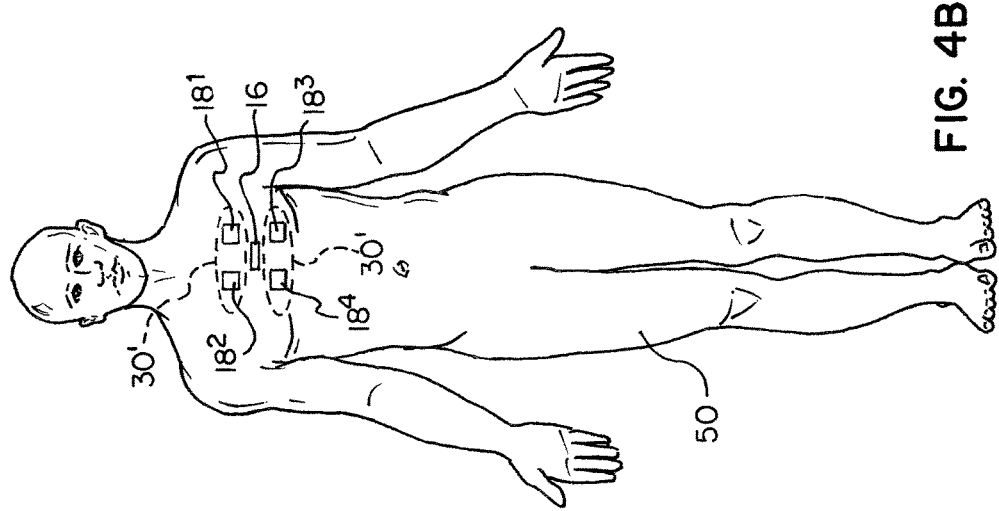
FIGS. 4A and 4B are schematic views illustrating various exemplary options for the placement on a patient of the electrodes of the device shown in FIG. 1.
Figure 4A:
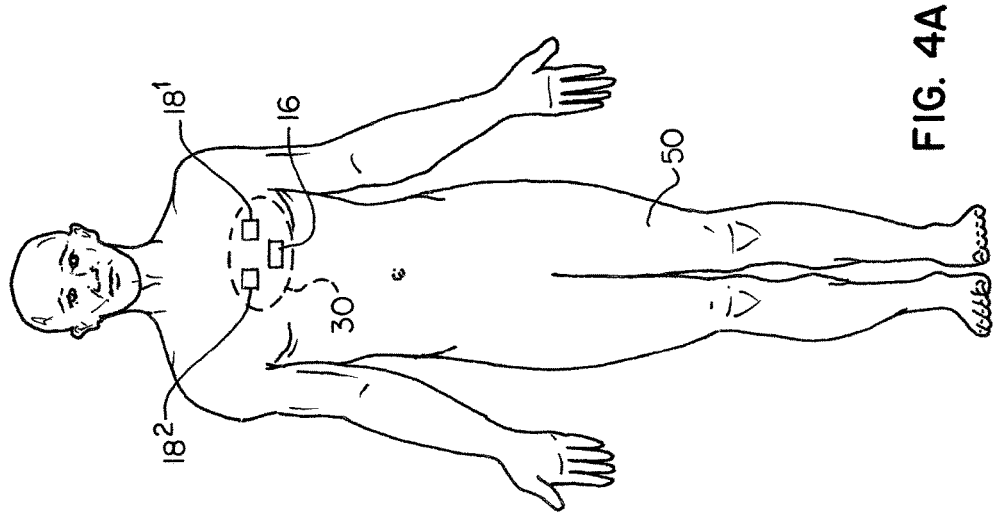

Turning now to FIGS. 4A and 4B, an exemplary positioning of electrodes ($18^1$ and $18^2$) on the patient (50) is shown. In this exemplary embodiment, a first electrode ($18^1$) supplies transcutaneous electrical impulses at a first frequency and a second electrode ($18^2$) supplies transcutaneous electrical impulses at a second frequency different than the first frequency, the transcutaneous electrical impulses provided at the first and second frequencies giving rise to a first beat impulse having a first interference frequency. The first and second electrodes ($18^1, 18^2$) are positioned such that the therapeutic target area thereof is positioned to cause stimulation of a first area of the heart and/or a first nerve associated with the heart with the first beat impulse having the first interference frequency as is explained in more detail below.

With respect specifically to FIG. 4B, a third electrode ($18^3$) supplies transcutaneous electrical impulses at a third frequency and a fourth electrode ($18^4$) supplies transcutaneous electrical impulses at a fourth frequency different than the third frequency, the transcutaneous electrical impulses provided at the third and fourth frequencies giving rise to a second beat impulse having a second interference frequency. The third and fourth electrodes ($18^3, 18^4$) are positioned such that the therapeutic target area thereof is positioned to cause stimulation of a second desired area of the heart and/or a second nerve associated with the heart with the second beat impulse having the second interference frequency as is explained in more detail below.

As will be understood by those skilled in the art, additional pairs of electrodes may be employed to produce additional beat impulses at the same or different beat frequencies as those described above, depending on the particular application of the device (10).

Each of the first pair of electrodes ($18^1, 18^2$) may be formed as a separate pad, or as illustrated in FIG. 4A, both electrodes ($18^1, 18^2$) may be disposed on a common pad (30) for ease of placement on the patient (50). In the example of FIG. 4A, the sensor (16) is also disposed on the same pad (30) for further ease of placement.

In the exemplary embodiment of FIG. 4B, both of the first pair of electrodes ($18^1, 18^2$) are disposed on a common pad (30') and both of the second pair of electrodes ($18^3, 18^4$) are disposed on another common pad (30') for ease of placement on the patient (50). In the example of FIG. 4B, however, the sensor (16) is disposed separately from the electrode carrying pads (30').

The pads (30,30") and/or the electrodes (18) may take any of numerous forms. In some cases, the pads/electrodes may be formed with an adhesive on one side, such that the pads/electrodes can be affixed to the patient's skin. If desired, the pads/electrodes can be incorporated into or onto to an article of clothing (e.g., a robe or vest), a surgical drape or the like, a medical device, such as a splint, cast or other immobilization device, a wheelchair, a hospital bed, etc. The pads/electrodes can also take the form of a thin, flexible electrical circuit, such as in the nature of a temporary tattoo formed of an electrically conductive material.

Figure 5:
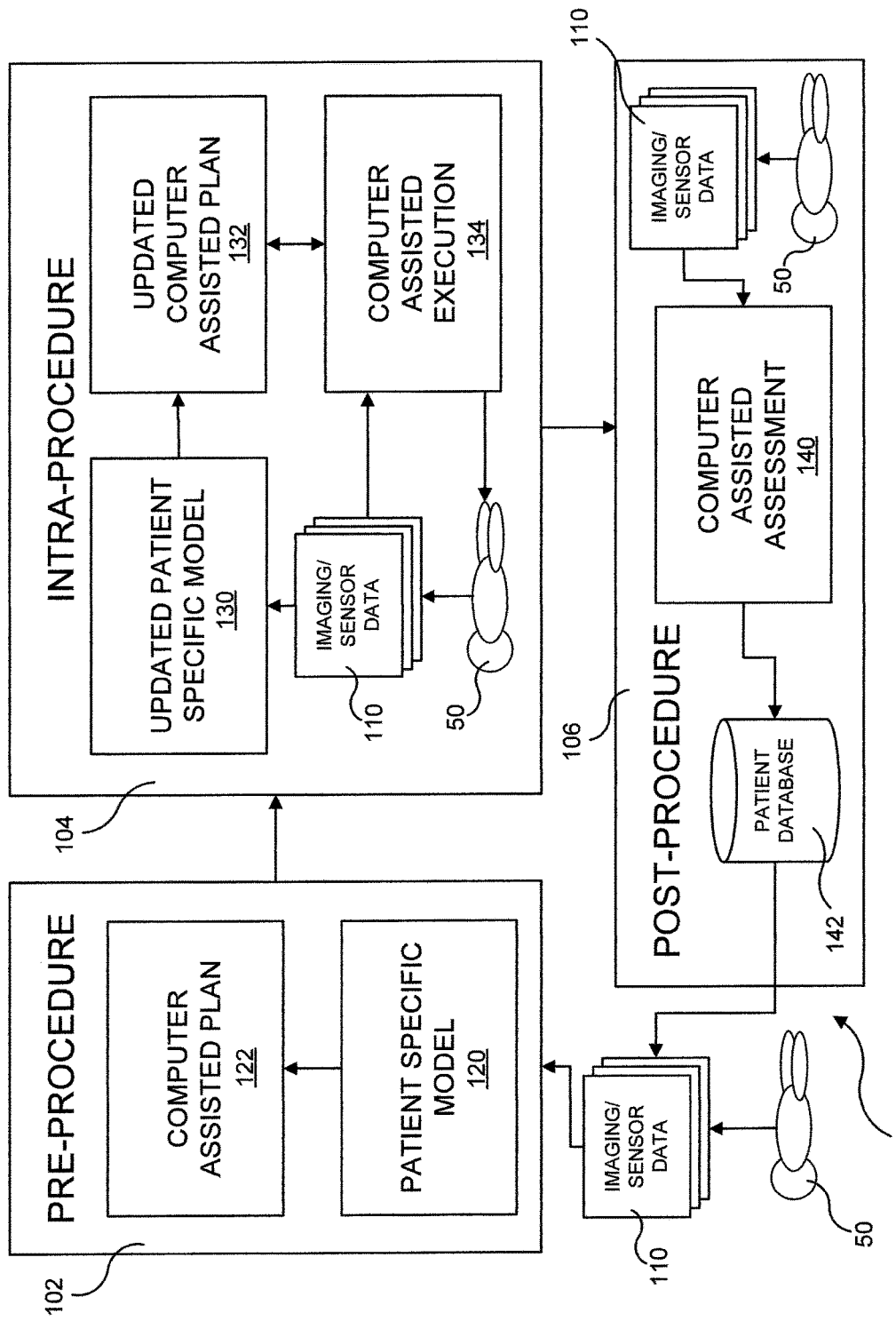
FIG. 5 is a schematic view illustrating an exemplary targeting scheme employed in the device shown in the system of FIG. 1.

Referring now to FIG. 5, a targeting aspect of the present invention is schematically shown. The goal of the targeting aspect of the present invention is to provide intelligent, versatile tools that augment the medical professional's ability to treat patients suffering from cardiac issues, both prior to and during the therapy.

As can be seen, the targeting system (100) shown in FIG. 5 can be broken down into three main stages: pre-procedure (102), intra-procedure (104) and post-procedure (106). A key aspect of all three stages is imaging/sensor data (110) collected from the patient (50), for example using the one or more sensors (16).

As will be recognized by those skilled in the art, different types of imaging/sensor data (110) may be employed, with there being many known and yet to be developed diagnostic modalities that may be appropriate.

For example, many imaging modalities are known that would be appropriate to collect imaging sensor data (110), including ultrasound (including Level II ultrasound, 3D ultrasound, 4D ultrasound, etc.), trans esophageal echogram (TEE), x-rays, computed tomography (CT) scanning, magnetic resonance imaging MRI scanning (3D or otherwise), positron emission tomography (PET), radiography, elastography, thermography, bone scanning, etc. More advanced imaging techniques involving combinations of various modalities may also be used.

The imaging modalities used may be static or dynamic. In addition, various functional modalities may be employed, such as Doppler ultrasound to measure blood flow through the heart and surrounding blood vessels, or other forms of plethsmethography (which is measurement of blood flow dynamics). Image intensification is another diagnostic modality that can be used, which affords x-ray assessment in real time with motion as in some of the ultrasound options. This can be important during procedures such as cardiac catheterizations.

Additionally, various other types of electrical sensor data may be used to assist with targeting of the IFC currents. For example, electrocardiography (EKG) and echocardiography (Echo) are both typically extremely important diagnostic tools when dealing with pacing, identification of ischemic areas of the heart and other cardiac issues.

The sensor(s) may be integrated with a robotics device, machine, or algorithm. Rather than using robotics to aid surgeons, the robotics technology can be combined with IFC to give extremely accurate microscopic and larger field targeting through the IFC. In fact, the robotics could be combined with IFC such that an individual could do essentially "IFC robotic surgery" in which the robotic assisted mechanism not only targets the area through robotic anatomic analysis, but then also, the robotic arms controlled by the medical practitioner would place the appropriate interferential electrodes on the skin and, through the connecting robotic arm, also supply the appropriate electric current with feedback through the robotic surgery targeting technology and device.

Instead or in addition, the sensor(s) may be integrated with a cellphone or other mobile device as the coordinating interface. This is envisioned as incorporating current cellphone apps that actually provide handheld diagnostic ultrasounds using either the cellphone camera mechanism or a program using the cellphone's screen. For example, there are cellphone apps currently being used by women to view their fetus at any time during pregnancy as opposed to having an actual formal ultrasound. In some cases, this type of mobile targeting device can, in the clinical setting, be easier to use than a currently employed ultrasound machine. Using such a cellphone app would include wireless transmission of the electrical impulses to the electrodes, or could even include a transducer connected to wires, which then plug into a port in either a computer or the cellphone, similar to the way music earplugs now transmit music from a cellphone either through wires or wireless headphones.

It should also be recognized that a combination of two or more of the above described, and/or other, techniques may be employed to collect the imaging/sensor data (110) employed by the targeting system (100).

As shown in FIG. 5, imaging/sensor data (110) is used in the pre-procedure stage (102) to generate a patient specific model (at 120), such as a three-dimensional model of the patient's heart. Of particular importance is locating on the model the one or more therapeutic target areas of the patient to be targeted with the IFC. This model is then used with other data in the memory (24) of device (10) to generate a computer assisted plan (at 122), including the location for initial placement of the electrodes (18), as well as data indicative of the frequencies of the interferential currents to be generated to create the beat impulse(s) having the interference frequency/frequencies desired for the particular application.

The electrodes (18) are positioned according to the computer assisted plan (122), and the IFC therapy procedure may be commenced. During the intra-procedure stage (104), additional imaging/sensor data (110) may continue to be collected from the patient (50), which data (110) may be used to update the patient specific model (at 130), for example, if changes to the patient's heart occur, and to update the computer assisted plan (at 132). For example, it may be determined that one or more of the electrodes (18) should be repositioned and/or that the frequencies of the interferential currents require adjustment so that the frequencies of the resulting beat impulse(s) are correspondingly adjusted.

Also, during the intra-procedure stage (104), computer assisted execution of the plan may be performed (at 134), for example, by the controller (12). Such execution may be performed automatically, manually in response to user input or automatically in part and manually in part. For example, the controller (12) may increase and/or decrease the frequencies of the resulting beat impulses automatically in real time in response to sensed conditions. It may also control the robotics previously mentioned, and it would be in communication with those targeting algorithms.

After the procedure is completed, in a post-procedure stage (106), imaging/sensor data (110) may continue to be collected, and then a computer assisted assessment may be performed (at 140) in order to generate data concerning the impact of the procedure on the patient (50). This data, which may be stored in a database (142) may be used in order to help with planning future procedures for the same patient (50) or with other patients, for example who will undergo similar procedures. For example, the data may be helpful in generating the computer assisted plan (122). As the targeting system requires altering the position of at least some of the electrodes, each relevant electrode is moved to a new position.

The data (110) can also be connected to and used with telehealth, electronic medical record (EMR), and offsite doctor transmission and analysis programs as part of the integration with advanced computer algorithms and trends in medical care.

Although the invention has been described with reference to particular arrangement of parts, features, and the like, these are not intended to exhaust all possible arrangements or features, and indeed many modifications and variations will be ascertainable to those of skill in the art.

What is claimed is:

1. An interferential current system for cardiac treatment of a patient, comprising:
    a controller;
    a stimulation power supply in communication with the controller;
    a plurality of electrodes in electrical communication with the stimulation power supply, wherein the plurality of electrodes supply transcutaneous electrical impulses when supplied power by the stimulation power supply, the plurality of electrodes comprising at least two electrodes supplying transcutaneous electrical impulses at two different frequencies, the transcutaneous electrical impulses provided at two different frequencies giving rise to at least one beat impulse having an interference frequency;
    a sensor in communication with the controller and providing data to the controller indicative of cardiac contractions of the patient;
    wherein at least one of a timing and an intensity of the transcutaneous electrical impulses is varied by the controller based at least in part upon the data indicative of cardiac contractions of the patient; and
    wherein the cardiac treatment comprises cardiac contractility modulation (CCM), and wherein the plurality of electrodes are disposed so as to stimulate heart contractions at predetermined times during a heartbeat cycle.

2. The system of claim 1 wherein the timing of the transcutaneous electrical impulses is varied based at least in part upon the data indicative of cardiac contractions of the patient such that electrical stimulation is applied to a cardiac muscle during an absolute refractory period of the heartbeat cycle.

3. The system of claim 1, wherein the controller generates a patient specific model based at least in part on the data indicative of cardiac contractions of the patient.

4. The system of claim 3, wherein the patient specific model is indicative of appropriate magnitudes of the at least two different frequencies.

5. The system of claim 3, wherein the patient specific model is indicative of the appropriate interference frequency.

6. The system of claim 1, wherein said plurality of electrodes comprises:
a first electrode supplying transcutaneous electrical impulses at a first frequency and a second electrode supplying transcutaneous electrical impulses at a second frequency different than the first frequency, the transcutaneous electrical impulses provided at the first and second frequencies giving rise to a first beat impulse having a first interference frequency stimulating a first area of a heart of the patient; and
a third electrode supplying transcutaneous electrical impulses at a third frequency and a fourth electrode supplying transcutaneous electrical impulses at a fourth frequency different than the third frequency, the transcutaneous electrical impulses provided at the third and fourth frequencies giving rise to a second beat impulse having a second interference frequency stimulating a second area of the heart of the patient.

7. An interferential current system for cardiac treatment of a patient, comprising:
a controller;
a stimulation power supply in communication with the controller;
a plurality of electrodes in electrical communication with the stimulation power supply, wherein the plurality of electrodes supply transcutaneous electrical impulses when supplied power by the stimulation power supply, the plurality of electrodes comprising at least two electrodes supplying transcutaneous electrical impulses at two different frequencies, the transcutaneous electrical impulses provided at two different frequencies giving rise to at least one beat impulse having an interference frequency;
a sensor in communication with the controller and providing data to the controller indicative of cardiac contractions of the patient;
wherein at least one of a timing and an intensity of the transcutaneous electrical impulses is varied by the controller based at least in part upon the data indicative of cardiac contractions of the patient;
wherein the controller generates a patient specific model based at least in part on the data indicative of cardiac contractions of the patient;
an imaging sensor, and
wherein the patient specific model is further based at least in part on imaging data received from the imaging sensor.

8. The system of claim 7, wherein the patient specific model is indicative of electrode placement appropriate for the transcutaneous electrical impulses to reach a desired therapeutic target area.

9. The system of claim 7, wherein the imaging sensor comprises an imaging sensor employing at least one of the following modalities: ultrasound, Level II ultrasound, 3D ultrasound, 4D ultrasound, trans esophageal echogram (TEE), x-rays, computed tomography (CT) scanning, magnetic resonance imaging (MRI) scanning, 3D magnetic resonance imaging (MRI) scanning, positron emission tomography (PET), radiography, elastography, plethsmethography, thermography, bone scanning and image intensification.

10. A method for cardiac treatment of a patient employing interferential current therapy, the method comprising the steps of:
disposing a plurality of electrodes on an epidermis of a patient;
supplying to a heart of the patient, with the plurality of electrodes, transcutaneous electrical impulses at two different frequencies, the transcutaneous electrical impulses provided at two different frequencies giving rise to at least one beat impulse having an interference frequency;
collecting sensor data indicative of cardiac contractions of the patient;
varying at least one of a timing and an intensity of the transcutaneous electrical impulses based at least in part upon the data indicative of cardiac contractions of the patient;
wherein the cardiac treatment comprises cardiac contractility modulation (CCM), and wherein the plurality of electrodes are disposed so as to stimulate heart contractions at predetermined times during a heartbeat cycle.

11. The method of claim 10 wherein the timing of the transcutaneous electrical impulses is varied based at least in part upon the data indicative of cardiac contractions of the patient such that electrical stimulation is applied to a cardiac muscle during an absolute refractory period of the heartbeat cycle.

12. The method of claim 10, further comprising the step of generating a patient specific model based at least in part on the data indicative of cardiac contractions of the patient.

13. A method for cardiac treatment of a patient employing interferential current therapy, the method comprising the steps of:
disposing a plurality of electrodes on an epidermis of a patient;
supplying to a heart of the patient, with the plurality of electrodes, transcutaneous electrical impulses at two different frequencies, the transcutaneous electrical impulses provided at two different frequencies giving rise to at least one beat impulse having an interference frequency;
collecting sensor data indicative of cardiac contractions of the patient;
varying at least one of a timing and an intensity of the transcutaneous electrical impulses based at least in part upon the data indicative of cardiac contractions of the patient;
generating a patient specific model based at least in part on the data indicative of cardiac contractions of the patient;
collecting imaging data from an imaging sensor, and
wherein the patient specific model is further based at least in part on the imaging data.

14. The method of claim 13, wherein the patient specific model is indicative of electrode placement appropriate for the transcutaneous electrical impulses to reach a desired therapeutic target area, and wherein the disposing step is performed based at least in part on the patient specific model.

* * * * *